United States Patent
Lull et al.

(10) Patent No.: US 10,052,277 B2
(45) Date of Patent: *Aug. 21, 2018

(54) EXTENDED RELEASE FRAGRANCE COMPOSITIONS

(71) Applicant: Avon Products, Inc., Suffern, NY (US)

(72) Inventors: Michael A. Lull, Pleasantville, NY (US); William E. McNamara, Chester, NY (US); Glen T. Anderson, Pleasantville, NY (US)

(73) Assignee: Avon Products, Inc., Rye, NY (US)

( * ) Notice: Subject to any disclaimer, the term of this patent is extended or adjusted under 35 U.S.C. 154(b) by 14 days.

This patent is subject to a terminal disclaimer.

(21) Appl. No.: 15/635,287

(22) Filed: Jun. 28, 2017

(65) Prior Publication Data

US 2017/0296454 A1  Oct. 19, 2017

Related U.S. Application Data

(63) Continuation of application No. 14/547,439, filed on Nov. 19, 2014, now Pat. No. 9,717,237, which is a continuation of application No. 14/165,687, filed on Jan. 28, 2014, now Pat. No. 8,921,303.

(51) Int. Cl.
| | |
|---|---|
| *A61Q 13/00* | (2006.01) |
| *A01N 25/04* | (2006.01) |
| *A61K 8/894* | (2006.01) |
| *A01N 27/00* | (2006.01) |
| *A01N 25/24* | (2006.01) |
| *A01N 65/00* | (2009.01) |
| *A61K 8/92* | (2006.01) |
| *A61K 8/81* | (2006.01) |
| *A61K 8/34* | (2006.01) |
| *A61K 8/04* | (2006.01) |

(52) U.S. Cl.
CPC .............. *A61K 8/894* (2013.01); *A01N 25/04* (2013.01); *A01N 25/24* (2013.01); *A01N 27/00* (2013.01); *A01N 65/00* (2013.01); *A61K 8/042* (2013.01); *A61K 8/34* (2013.01); *A61K 8/345* (2013.01); *A61K 8/8152* (2013.01); *A61K 8/922* (2013.01); *A61Q 13/00* (2013.01); *A61K 2800/262* (2013.01); *A61K 2800/42* (2013.01); *A61K 2800/48* (2013.01)

(58) Field of Classification Search
CPC ....................................................... A61K 8/894
See application file for complete search history.

(56) References Cited

U.S. PATENT DOCUMENTS

| | | |
|---|---|---|
| 4,874,129 A | 10/1989 | Disapio |
| 5,176,903 A | 1/1993 | Goldberg et al. |
| 5,437,867 A | 8/1995 | Vichroski et al. |
| 6,346,256 B1 | 2/2002 | Pascal |
| 6,379,689 B1 | 4/2002 | Aguadisch |
| 6,932,982 B2 | 8/2005 | Melver et al. |
| 6,936,686 B2 | 8/2005 | Awad |
| 7,294,612 B2 | 11/2007 | Popolewell et al. |
| 8,349,338 B2 | 1/2013 | Loginova et al. |
| 2001/0027213 A1 | 10/2001 | Seki et al. |
| 2007/0196291 A1 | 8/2007 | Sakuta |
| 2008/0145436 A1* | 6/2008 | Lorant ............... A61K 8/064 424/489 |
| 2009/0025805 A1 | 10/2009 | Thomas et al. |
| 2012/0058973 A1 | 3/2012 | Narashimhan et al. |
| 2012/0237464 A1 | 9/2012 | Ahn et al. |
| 2013/0003996 A1 | 2/2013 | Gonzales et al. |
| 2013/0243835 A1 | 9/2013 | Tanner et al. |

FOREIGN PATENT DOCUMENTS

| | | |
|---|---|---|
| CN | 101810565 A | 8/2010 |
| EP | 1704853 A2 | 9/2006 |
| WO | 200243491 A1 | 6/2002 |
| WO | 2007/024978 A2 | 3/2007 |

OTHER PUBLICATIONS

Extended EP Search Report to corresponding EP Application No. 14880438.8 dated Jun. 19, 2017 (11 pages).

* cited by examiner

*Primary Examiner* — Gina C Justice

(74) *Attorney, Agent, or Firm* — Brian P. McCloskey

(57) ABSTRACT

Compositions are provided that provide release of fragrance over an extended period of time. The compositions comprise a hydrophilically-modified cross-linked silicone elastomer and an acrylic rheology modifier.

12 Claims, 1 Drawing Sheet

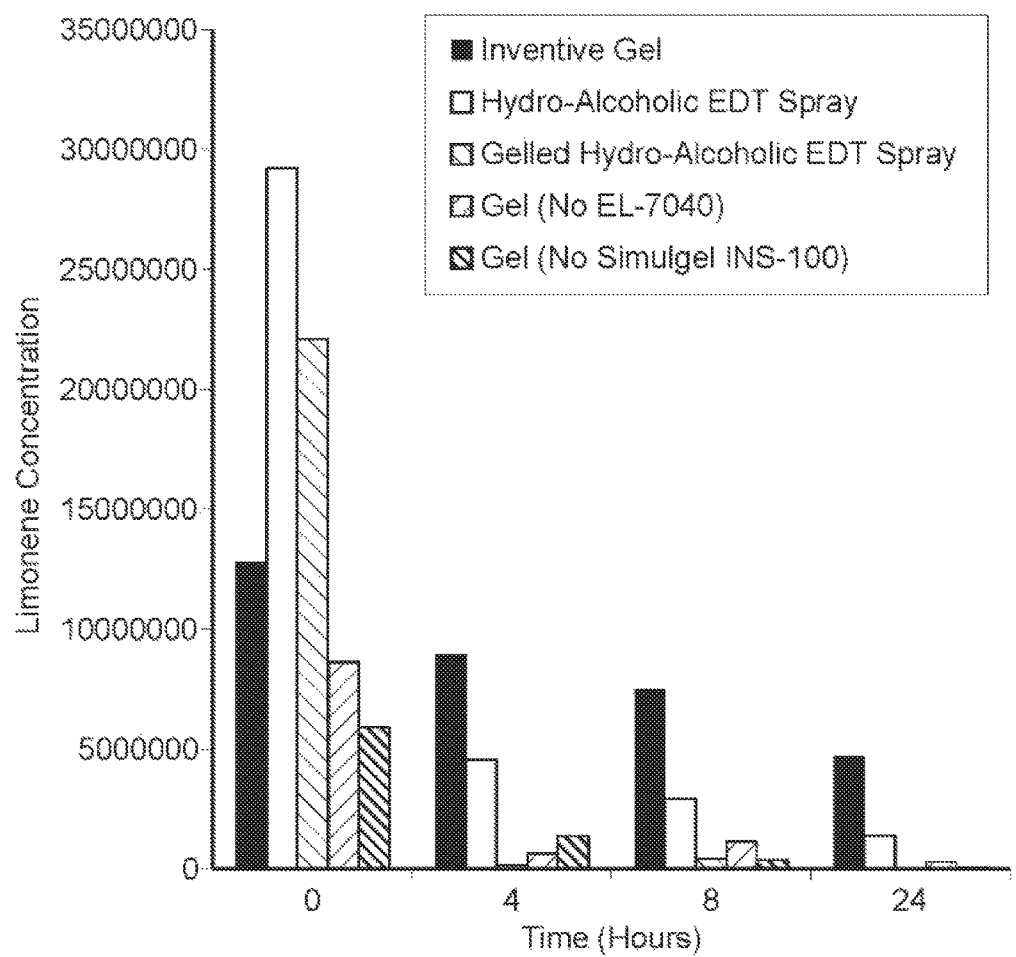

EXTENDED RELEASE FRAGRANCE COMPOSITIONS

CROSS-REFERENCE TO RELATED APPLICATIONS

This application is a continuation of and claims priority to U.S. Nonprovisional patent application Ser. No. 14/547,439 filed Nov. 19, 2014 and U.S. Nonprovisional patent application Ser. No. 14/165,687 filed Jan. 28, 2014, U.S. Pat. No. 8,921,303 granted Dec. 30, 2014, which are hereby fully incorporated by reference in its entirety for all purposes.

FIELD OF INVENTION

The invention relates generally to compositions comprising a hydrophilically-modified cross-linked silicone elastomer and an acrylic rheology modifier which provide release of fragrance over an extended period of time.

BACKGROUND OF THE INVENTION

It is well known in the fragrance arts that scents deposited on surfaces such as keratinous surfaces of the body, lose intensity over time. Many attempts have therefore been made to increase the amount of time that fragrances remain on such surfaces without increasing fragrance load. For example, those in the field have attempted to increase fragrance retention time through the use of various coatings and microencapsulation systems. (See, e.g., U.S. Pat. Nos. 7,294,612; 6,932,982; and 5,176,903; each of which is hereby incorporated by reference in its entirety). Despite these techniques, there is an ongoing need in the art for improved compositions that can extend the duration of fragrance release without necessarily increasing the amount of fragrance used.

It is therefore an object of the invention to provide compositions that provide extended release of fragrance, and to provide methods that provide prolonged delivery of a fragrance from a surface, such as a human integument.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, compositions are provided that release fragrance over an extended period of time. It has surprisingly been found that compositions comprising a combination of a hydrophilically-modified cross-linked silicone elastomer and an acrylic rheology modifier, can provide a synergistic improvement in the retention of a fragrance oil such that fragrance is released over a longer period of time.

The compositions are typically in the form of a clear or translucent gel. The compositions may comprise from about 0.5% to about 5% by weight of a hydrophilically-modified cross-linked silicone elastomer, such as those comprising poly(alkylene oxide) chains grafted to a silicone backbone (e.g., PEG-12 dimethicone/PPG-20 crosspolymer), and from about 0.5% to about 5% by weight of an acrylic rheology modifier, such as copolymers of an acrylate monomer and an acrylamide monomer (e.g., hydroxyethyl acrylate/sodium acryloyldimethyltaurate copolymer). The weight ratio of the hydrophilically-modified cross-linked silicone elastomer and the acrylic rheology modifier will typically range from about 10:1 to about 1:10, more typically from about 2:1 to about 1:2 (e.g., about 1:1). In addition, the compositions may comprise a polyol (e.g., glycerin), for example, in an amount from about 35% to about 50% by weight, and an alcohol (e.g., ethanol), for example in an amount from about 35% to about 50% by weight. The compositions also comprise a fragrance oil (or blend of fragrance oils) which will typically comprise from about 0.5% to about 25% by weight of the composition, more typically from about 2% to about 10% by weight of the composition (e.g., about 5% by weight of the composition). The compositions optionally comprise one or more actives, such as, for example, retinoids, hydroxyl acids, depigmenting agents, botanicals, collagenase inhibitors, elastase inhibitors, sunscreens, anti-perspirants, deodorants, anti-bacterials, and anti-fungals. The compositions may be either hydrous or anhydrous. The compositions may also optionally comprise one or more colorants (e.g., pigments, lakes, dyes, etc.). The compositions of the invention are capable of releasing the fragrance oil over a longer period of time as compared to otherwise identical compositions that lack either the hydrophilically-modified cross-linked silicone elastomer or the acrylic rheology modifier. The combination of the hydrophilically-modified cross-linked silicone elastomer and the acrylic rheology modifier may result in a synergistic improvement in the duration of release of a fragrance oil from the compositions. The fragrance oil may be an oil that is used for primarily aesthetic benefits (e.g., a perfume) or may have functional benefits (e.g., an insect repellant such as citronella oil). Also provided are methods for providing prolonged delivery of a fragrance oil, comprising applying to a surface (e.g., a human integument such as skin of the face or body), a composition of the invention.

These and other aspects of the present invention will become apparent to those skilled in the art after a reading of the following detailed description of the invention, including the appended claims.

BRIEF DESCRIPTION OF THE DRAWINGS

FIG. 1 shows the results of an experiment assessing fragrance retention time for several different fragrance compositions over a 24 hour period, as determined by gas chromatography analysis of headspace.

DETAILED DESCRIPTION

All amounts provided in terms of weight percentage are relative to the entire composition unless otherwise stated. It will be understood that the total of all weight percentages in a given composition will not exceed 100%.

The present invention is founded on the discovery that compositions comprising combinations of hydrophilically-modified cross-linked silicone elastomers and acrylic rheology modifiers provide an unexpected improvement (preferably, a synergistic improvement) in the duration of release of a fragrance oil from the compositions. By "synergistic improvement" is meant that a composition comprising a combination of a hydrophilically-modified cross-linked silicone elastomer and an acrylic rheology modifier, results in a duration of fragrance oil release that is greater than the additive effect that the same two components separately have on the duration of fragrance oil release.

The compositions of the invention comprise a hydrophilically-modified cross-linked silicone elastomer in an amount from about 0.1% to about 25% by weight, or from about 0.2% to about 20% by weight, or from about 0.3% to about 15% by weight of the composition. More typically, the compositions comprise a hydrophilically-modified cross-linked silicone elastomer in an amount from about 0.5% to about 10%, from about 0.5% to about 5%, or from about 1% to about 3% by weight of the composition. In one preferred embodiment, the hydrophilically-modified cross-linked silicone elastomer comprises about 1.5% by weight of the composition.

Suitable hydrophilically-modified cross-linked silicone elastomers are preferably capable of forming a gel with a polyol and/or alcohol. Such elastomers may comprise poly(alkylene oxide) chains grafted to a silicone backbone. In one preferred embodiment, the hydrophilically-modified cross-linked silicone elastomer comprises PEG-12 dimethicone/PPG-20 crosspolymer.

Other suitable hydrophilically-modified cross-linked silicone elastomers include those described in U.S. Patent Application Publication No. 2013/0005832, hereby incorporated by reference in its entirety. For example, suitable polyoxyalkylenated silicone elastomers include those sold by Shin-Etsu as "KSG-21," "KSG-20," "KSG-3," "KSG-31," "KSG-32," "KSG-33," "KSG-210," "KSG-310," "KSG-320," "KSG-330," "KSG-340," and "X-226146," and those sold by Dow Corning as "DC9010" and "DC9011." Other useful hydrophilically-modified cross-linked silicone elastomers include those described in U.S. Pat. Nos. 5,236,986; 5,412,004; 5,837,793; and 5,811,487, the content of each of which is hereby incorporated by reference in its entirety.

Additional suitable hydrophilically-modified cross-linked silicone elastomers include those described in U.S. Patent Application Publication No. 2005/0220728, hereby incorporated by reference in its entirety. For example, suitable polyglycerolated silicone elastomers include those sold by Shin-Etsu as "KSG-710," "KSG-810," "KSG-820," "KSG-830," and "KSG-840."

Additional suitable hydrophilically-modified cross-linked silicone elastomers include those described in U.S. Pat. No. 6,524,598, hereby incorporated by reference in its entirety.

The compositions of the invention comprise an acrylic rheology modifier in an amount from about 0.1% to about 25% by weight, or from about 0.2% to about 20% by weight, or from about 0.3% to about 15% by weight of the composition. More typically, the compositions comprise an acrylic rheology modifier in an amount from about 0.2% to about 10%, from about 0.5% to about 5%, or from about 1% to about 3% by weight of the composition. In one preferred embodiment, the acrylic rheology modifier comprises about 1.5% by weight of the composition.

Suitable acrylic rheology modifiers are preferably those that are capable of forming a gel with a suitable solvent such as a polyol and/or an alcohol. Such acrylic rheology modifiers will include homo and copolymers of acrylic or acrylate monomers. In one embodiment, the acrylic rheology modifier comprises copolymers of an acrylate monomer and an acrylamide monomer. In one preferred embodiment, the acrylic rheology modifier comprises hydroxyethyl acrylate/sodium acryloyldimethyltaurate copolymer.

Other useful acrylic rheology modifiers include those described in U.S. Patent Application Publication No. 2013/0130959, hereby incorporated by reference in its entirety. For example, these include ViscUp® EZ (INCI name Sodium Acrylate/Sodium Acryloyldimethyl Taurate Copolymer & Hydrogenated Polydecene & Sorbitan Laurate & Trideceth-6) marketed by Arch Personal Care Products; and those sold by SEPPIC as Sepiplus S (hydroxyethyl acrylate sodium acryloyldimethyl taurate copolymer and polyisobutene and PEG-7 trimethyloylpropane coconut ether); Sepinov EMT 10 (hydroxyethyl acrylate sodium acryloyldimethyl taurate copolymer); and Simulgel 600 (acrylamide/sodium acryloyldimethyltaurate copolymer/isohexadecane/polysorbate 80).

Additional suitable acrylic rheology modifiers include the anionic thickeners described in U.S. Patent Application Publication No. 2208/0196174, incorporated by reference herein in its entirety. These include, without limitation, those comprising 2-acrylamido-2-methyl propane sulfonic acid monomers. The thickeners described in U.S. Patent Application Publication No. 2004/0028637, hereby incorporated by reference in its entirety, are also contemplated to be useful.

Other useful acrylic rheology modifiers include those described in U.S. Pat. No. 6,524,598, hereby incorporated by reference in its entirety. For example, these include those sold by B.F. Goodrich Co. as Carbopol 934, Carbopol 940, Carbopol 950, Carbopol 980, Carbopol 951, Carbopol 981, Carbopol Ultrez 10, Carbopol ETD2020, Carbopol 1382, and Carbopol 1342, as well as Pemulen TR-1, sold by Lubrizol.

In one embodiment, the composition is in the form of a gel that is formed by the hydrophilically-modified cross-linked silicone elastomer, acrylic rheology modifier, polyol, and alcohol.

In one embodiment, the composition is free of additional gelling agents other than the hydrophilically-modified cross-linked silicone elastomer and the acrylic rheology modifier. In another embodiment, the composition may comprise additional gelling agents, but in amounts insufficient to form a gel in the absence of the hydrophilically-modified cross-linked silicone elastomer and acrylic rheology modifier.

In some embodiments, additional gelling agents or rheology modifiers, if present, will be included at a level of less than about 0.5% by weight or less than about 0.1% by weight of the total composition. In another embodiment, the composition is substantially free of additional gelling agents or rheology modifiers, by which is meant that any additional gelling agents of rheology modifiers when present, are at levels so low that they do not measurably impart viscosity or structure to the composition.

The compositions may be anhydrous, substantially anhydrous, or may comprise water. By "substantially anhydrous" is meant that no water is intentionally added to the composition, and only those amounts of water typically associated with the raw ingredients (e.g., due to the hygroscopic nature of glycerin and alcohol) are included. In some embodiments, the compositions will comprise less than about 5% by weight water, or less than about 2% by weight water, or less than about 1% by weight water, or less than about 0.5% by weight water.

The weight ratio of the hydrophilically-modified cross-linked silicone elastomer and the acrylic rheology modifier will typically range from about 10:1 to about 1:10, or from about 8:1 to about 1:8, or from about 5:1 to about 1:5, and more typically from about 2:1 to about 1:2. In one preferred embodiment, the weight ratio of the hydrophilically-modified cross-linked silicone elastomer and the acrylic rheology modifier is from about 1:1.

The compositions of the invention typically comprise a polyol, for example in an amount from about 20% to about 75%, or from about 25% to about 65% by weight of the composition, or more typically in an amount from about 35% to about 50% or from about 40% to about 50% by weight of the composition. In one preferred embodiment, the polyol will comprise about 45% by weight of the composition.

Suitable polyols for inclusion in the compositions include, without limitation, $C_{2-6}$ polyols such as ethylene glycol, propylene glycol, butylene glycol, hexylene glycol, sorbitol, diethylene glycol, and glycerin. In one preferred embodiment, the polyol comprises glycerin.

The compositions of the invention also typically comprise an alcohol, for example in an amount from about 20% to about 75%, or from about 25% to about 65% by weight of the composition, or more typically comprise from about 35% to about 50% or from about 40% to about 50% by weight of the composition. In one preferred embodiment, the alcohol comprises about 45% by weight of the composition.

Any alcohol can be used in the compositions of the invention, but preferably the alcohol is a low order alcohol, such as ethanol, methanol, n-propanol, isopropanol, n-butanol, isobutanol, and tert-butanol. In one preferred embodiment, the alcohol comprises ethanol.

The weight ratio of the polyol to the alcohol will typically range from about 10:1 to about 1:10, or from about 5:1 to about 1:5, or from about 2:1 to about 1:2, or about 1:1.

The compositions also comprise a fragrance oil (or blend of fragrance oils) which will typically comprise from about 0.5% to about 25%, from about 1% to about 20%, from about 3% to about 15%, from about 5% to about 10%, and more typically from about 2% to about 8% by weight of the composition. In one preferred embodiment, a fragrance oil comprises about 5% by weight of the composition.

Any fragrance oil can be used in the compositions of the invention, such as those described in U.S. Patent Application Publication No. 2013/0280409, hereby incorporated by reference in its entirety. For example, the fragrance oil may include any one or more of extracts of natural raw materials such as essential oils, concretes, absolutes, resins, resinoids, balsams, tinctures such as, for example, ambergris tincture; amyris oil; *angelica* seed oil; *angelica* root oil; aniseed oil; valerian oil; basil oil; wood moss absolute; bay oil; mugwort oil; benzoin resin; bergamot oil; beeswax absolute; birch tar oil; bitter almond oil; savory oil; bucco-leaf oil; cabreuva oil; cade oil; calamus oil; camphor oil; *cananga* oil; cardamom oil; cascarilla oil; *cassia* oil; *cassia* absolute; castoreum absolute; cedar-leaf oil; cedarwood oil; cistus oil; citronella oil; lemon oil; copaiba balsam; copaiba balsam oil; coriander oil; costus root oil; cumin oil; cypress oil; davana oil; dill oil; dillseed oil; eau de brouts absolute; oakmoss absolute; elemi oil; tarragon oil; *eucalyptus citriodora* oil; *eucalyptus* oil; fennel oil; fir oil; *galbanum* oil; *galbanum* resin; geranium oil; grapefruit oil; guaiac wood oil; gurjun balsam; gurjun balsam oil; helichrysum absolute; helichrysum oil; ginger oil; iris root abolute; iris root oil; jasmine absolute; calamus oil; blue camomile oil; Roman camomile oil; carrot-seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; *litsea cubeba* oil; bay-leaf oil; mace oil; marjoram oil; mandarin oil; massoi bark oil; *mimosa* absolute; ambrette oil; tincture of musk; clary sage oil; *myristica* oil; myrrh absolute; myrrh oil; myrtle oil; clove leaf oil; clove flower oil; neroli oil; olibanum abolute; olibanum oil; opopanax oil; orange blossom absolute; orange oil; *origanum* oil; palmarosa oil; patchouli oil; *perilla* oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike lavender oil; Japanese aniseed oil; *styrax* oil; *tagetes* oil; fir-needle oil; tea-tree oil; turpentine oil; thyme oil; Tolu balsam; tonka absolute; tuberose absolute; vanilla extract; violet leaf absolute; *verbena* oil; vetiver oil; juniper oil; wine-lees oil; wormwood oil; wintergreen oil; ylang oil; hyssop oil; civet absolute; cinnamon leaf oil; cinnamon bark oil; as well as fractions thereof or constituents isolated therefrom; and combinations thereof.

Additional suitable fragrances, as listed in European Patent No. EP2106704B1, include, for example, any one or more of hydrocarbons, such as 3-carene; α-pinene; β-pinene; α-terpinene; γ-terpinene; p-cymene; bisabolene; camphene; caryophyllene; cedrene; farnesene; liminene; longifolene; myrcene; ocimene; valencene; (E,Z)-1,3,5-undecatriene;

Aliphatic alcohols, such as hexanol; octanol; 3-octanol; 2,6-dimethylheptanol; 2-methylheptanol; 2-methyl octanol; (E)-3-hexenol; (E) and (Z)-3-hexenol; 1-octen-3-ol; mixtures of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

Alphatic aldehydes and their acetals, such as hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;

Aliphatic ketones and oximes thereof, such as 2-heptanone; 2-octanone; 3-octanone; 2-nonanone; 5-methyl-3-heptanone; 5-methyl-3-heptanone oxime; 2,4,4,7-tetramethyl-6-octen-3-one;

Aliphatic sulphur-containing compounds, such as 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

Aliphatic nitriles, such as 2-nonenenitrile; 2-tridecenenenitrile; 2,12-tridecenenenitrile; 3,7-dimethyl-2,6-octadienenitrile; 3,7-dimethyl-6-octenenitrile;

Aliphatic carboxylic acids and esters thereof, such as (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl-2-isoamyloxyacetate; methyl-3,7-dimethyl-2,6-octadienoate;

Acyclic terpene alcohols, such as citronellol; geraniol; nerol; linalool; lavandulol; nerolidol; farnesol; tetrahydrolinalool; tetrahydrogeraniol; 2,6-dimethyl-7-octen-2-ol; 2,6-dimethyl octan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;

Acyclic terpene aldehydes and ketones, such as geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

Cyclic terpene alcohols, such as menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates, 3-methyl-2-butenoates thereof;

Cyclic terpene aldehydes and ketones, such as menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedarwood oil (methyl cedryl ketone);

Cyclic alcohols, such as 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

Cycloaliphatic alcohols, such as alpha-3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-timethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

Cyclic and cycloaliphatic ethers, such as cineol; cedryl methyl ether; cyclododecyl methyl ether; (ethoxymethoxy)cyclododecane; alpha-cedrene epoxide; 3a,6,6,9a-tetramethyl-dodecahydronaphtho[2,1-b]furan; 3a-ethyl-6,6,9a-trimethyldodecahydro-naphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

Cyclic ketones, such as 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 9-cycloheptadecen-1-one; cyclopentadecanone; cyclohexadecanone;

Cycloaliphatic aldehydes, such as 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

Cycloaliphatic ketones, such as 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert.-butyl (2,4-dimethyl-3-cyclohexen-1-yl) ketone;

Esters of cyclic alcohols, such as 2-tert.-butylcyclohexyl acetate; 4-tert.-butyl cyclohexyl acetate; 2-tert.-pentylcyclohexyl acetate; 4-tert.-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

Esters of cycloaliphatic carboxylic acids, such as allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

Aromatic hydrocarbons, such as styrene and diphenylmethane;

Araliphatic alcohols, such as benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

Esters of araliphatic alcohols and aliphatic carboxylic acids, such as benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha, alpha-dimethylphenylethyl acetate; alpha,alpha-dimethylphenylethyl butyrate; cinnamyl acetate; 2-phenoxyethyl isobutyrate; 4-methoxybenzyl acetate; araliphatic ethers such as for example 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a, 5,9b-tetrahydroindeno[1,2-d]-m-dioxin; 4,4a,5,9b-tetrahydro-2,4-dimethylindeno[1,2-d]-m-dioxin;

Aromatic and araliphatic aldehydes, such as benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

Aromatic and araliphatic ketones, such as acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methyl ethyl)-1H-5-indenyl]ethanone; 5',6',7',8'-tetrahydro-3',5',5',6',8',8'-hexamethyl-2-acetonaphthone;

Aromatic and araliphatic carboxylic acids and esters thereof, such as acid; phenylacetic acid; methyl benzoate; ethyl benzoate; hexyl benzoate; benzyl benzoate; methyl phenylacetate; ethyl phenylacetate; geranyl phenylacetate;

phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

Nitrogen-containing aromatic compounds, such as 2,4,6-trinitro-1,3-dimethyl-5-tert.-butylbenzene; 3,5-dinitro-2,6-dimethyl-4-tert.-butylacetophenone; cinnamonitrile; 5-phenyl-3-methyl-2-pentenenitrile; 5-phenyl-3-methylpentanenitrile; methyl anthranilate; methyl N-methylanthranilate; Schiff bases of methyl anthranilate with 7-hydroxy-3,7-dimethyloctanal; 2-methyl-3-(4-tert.-butylphenyl)propanal or 2,4-dimethyl-3-cyclohexenecarbaldehyde; 6-isopropylquinoline; 6-isobutylquinoline; 6-sec.-butylquinoline; indole; skatole; 2-methoxy-3-isopropylpyrazine; 2-isobutyl-3-methoxypyrazine;

Phenols, phenyl ethers and phenyl esters, such as estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

Heterocyclic compounds, such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one; and Lactones, such as 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Other suitable fragrance oils are those listed in U.S. Patent Application Publication Nos. 2012/0107529 and 2013/0202788, and U.S. Pat. No. 7,294,612, which are incorporated by reference in their entirety herein.

The compositions of the invention may also be formulated as insect repellant compositions that provide extended release of an insect repellant oil. The compositions may comprise any insect repellant oil or oils, including, for example, essential oils of citronella, catnip, and lavender; neem seed oil, and soy oil. Other suitable insect repellant oils are those listed in PCT Application Publication No. WO/2003013243; U.S. Pat. No. 8,501,205; and U.S. Published Application No. 2013/0084347, which are incorporated by reference in their entirety herein. These include, without limitation, lemongrass oil, rose geranium oil, lemon *eucalyptus* oil, and *litsea cubeba* oil, camphor, mineral oil, and geranium oil. As used herein, the term "fragrance oil" is intended to include insect repellant oils.

The compositions of the invention are useful for application to the human integumentary system, including, skin, lips, nails, hair, and other keratinous surfaces. As used herein, the term "keratinous surface" refers to keratin-containing portions of the human integumentary system, which includes, but is not limited to, skin, lips, hair (including eyebrows and eyelashes, hair of the scalp, facial hair, and body hair such as hair of the arms, legs, etc.), and nails (toenails, fingernails, cuticles, etc.) of mammalians, preferably humans.

In some embodiments, the compositions of the invention are in the form of a clear or translucent gel. The compositions may take the form of semi-solid, non-flowable, or flowable gels. In other embodiments, the compositions of the invention may be formulated as a cream, ointment, paste, foam, lotion, or stick.

It has been advantageously found that the compositions provide a moisturizing benefit to skin, due to the high level of humectant (polyol) and thus do not dry skin as might be expected from an alcohol-containing gel.

The compositions of the invention may be used in any suitable personal care product, such as perfumes, skincare products, including without limitation, body washes, face washes, body oils, body lotions or creams, anti-aging creams or lotions, body gels, day creams or lotions, night creams or lotions, treatment creams, skin protection ointments, moisturizing gels, body milks, suntan lotions, suntan creams, self-tanning creams, artificial tanning compositions, cellulite gels, peeling preparations, facial masks, depilatories, shaving creams, deodorants, anti-perspirants, and the like, particularly for topical administration.

In some embodiments, the compositions are used in hair products such as hair gels, mousses, sculpting and fixative products, and the like.

The compositions of the invention can be used in any suitable cosmetic, including color cosmetics or cosmetics without color.

Suitable colorants include those such as dyes, pigments and lakes. As used herein, the term "pigments" embraces lakes and fillers such as talc, calcium carbonate, etc. Exemplary inorganic pigments include, but are not limited to, inorganic oxides and hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO) and iron hydroxides including red iron oxide, yellow iron oxide and black iron oxide, titanium dioxide, titanium lower oxides, zirconium oxides, chromium oxides, chromium hydroxides, manganese oxides, manganese hydroxides, cobalt oxides, cobalt hydroxides, cerium oxides, cerium hydroxides, nickel oxides, nickel hydroxides, zinc oxides and zinc hydroxides and composite oxides and composite hydroxides such as iron titanate, cobalt titanate and cobalt aluminate and the like. The inorganic oxide particles may be selected from, for example, silica, alumina, zinc oxide, iron oxide and titanium dioxide particles, and mixtures thereof. In one embodiment, the pigments have a particle size from 5 nm to 500 microns, or from 5 nm to 250 microns, or from 10 nm to 100 microns. In some embodiments, the particle size (median) will be less than bout 5 microns or less than 1 micron.

Additional exemplary color additive lakes include, for example: D&C Red No. 19 (e.g., CI 45170, CI 73360 or CI 45430); D&C Red No. 9 (CI 15585); D&C Red No. 21 (CI 45380); D&C Orange No. 4 (CI 15510); D&C Orange No. 5 (CI 45370); D&C Red No. 27 (CI 45410); D&C Red No. 13 (CI 15630); D&C Red No. 7 (CI 15850:1); D&C Red No. 6 (CI 15850:2); D&C Yellow No. 5 (CI 19140); D&C Red No. 36 (CI 12085); D&C Orange No. 10 (CI 45475); D&C Yellow No. 19 (CI 15985); FD&C Red #40 (CI#16035); FD&C Blue #1 (CI#42090); FD&C Yellow #5 (CI#19140); or any combinations thereof.

In some embodiments, goniochromatic colorants (color travel pigments) are added to the clear or translucent gels of the invention, to provide a unique visual effect on the skin. Goiochromatic colorants have a platelet-shaped base substrate and are coated with alternating layers of high and low refractive index materials. For example, goniochromatic pigments such as Reflecks Pinpoints of Pearl pigments (calcium sodium borosilicate base coated with titanium dioxide and tin dioxide) sold by BASF may be used in the compositions, which have a particle size between about 4 and about 190 μm. The amount of goniochromatic pigment can be, for example, in an amount from about 0.1% to about 5%, and more preferably between about 0.25% and about 4.5% by weight of the total composition.

Suitable fillers may include talc, silica, alumina, zinc stearate, mica, kaolin, nylon (in particular orgasol) powder, polyethylene powder, polypropylene powder, acrylates powders, Teflon, starch, boron nitride, copolymer microspheres such as Expancel (Nobel Industrie), Polytrap (Dow Corning), and silicone resin microbeads (Tospearl from Toshiba).

Other fillers that may be used in the compositions of the invention include inorganic powders such as chalk, fumed silica, fumed alumina, calcium oxide, calcium carbonate, magnesium oxide, magnesium carbonate, Fuller's earth, attapulgite, bentonite, muscovite, phlogopite, synthetic mica, lepidolite, hectorite, biotite, lithia mica, vermiculite, aluminum silicate, aluminum magnesium silicate, diatomaceous earth, starch, alkyl and/or trialkyl aryl ammonium smectites, chemically modified magnesium aluminum silicate, organically modified montmorillonite clay, hydrated aluminum silicate, hydrated silica, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicon dioxide; organic powder, cyclodextrin, methyl polymethacrylate powder, copolymer powder of styrene and acrylic acid, benzoguanamine resin powder, and poly(ethylene tetrafluoride) powder.

The compositions may include natural or synthetic film-forming polymers. Suitable polymeric film formers include polyolefins, silicone polymers (e.g., dimethicones, dimethiconols, amodimethicones, silicone resins, etc.), (meth)acrylates, alkyl (meth)acrylates, polyurethanes, fluoropolymers, silicone polyurethanes, and silicone acrylates such as acrylates/dimethicone copolymers. In some embodiments, it may be desirable to add a hydrophilic or water-soluble film former (e.g., cellulosics, polysaccharides, polyquaterniums (such as polyquaternium-37 (INCI), etc.) to the composition to improve spreading, emulsion stability, aesthetic look and feel, etc. Elastomers formed from ethylene, propylene, butylene, and/or styrene monomers may also be useful.

The compositions of the invention may comprise any conventional cosmetic components, including pigments and colorants, fillers and cosmetic powders, film formers, additional gelling agents, thickeners, conditioners, actives, solvents, emulsifiers, humectants, emollients, pH adjusters, antioxidants, preservatives, and the like.

The compositions of the invention may include a cosmetically or dermatologically acceptable vehicle, which may be in the form of, for example, a serum, a cream, a lotion, a gel, or a stick, and may comprise an emulsion (e.g., water-in-oil, oil-in-water, water-in-silicone, silicone-in-water, polyol-in-silicone, silicone-in-polyol emulsion, etc.), or may comprise an aqueous or ethanolic vehicle, silicone (e.g., cyclomethicone, dimethicone, etc.), hydrocarbon (e.g., petrolatum, isododecane, etc.), ester oil (isopropyl myristate, myristyl myristate, or the like. The vehicle may be anhydrous and may comprise oils, such as dimethicones, hydrocarbons (e.g., isododecane), petrolatum, ester oils, and the like. The vehicle may further comprise an emulsifier, gelling agent, structuring agent, rheology modifier (e.g., a thickener), film former, or the like. The vehicle may comprise from about 25% to about 99% by weight of the composition.

The compositions may further include an emulsifier. The amount of emulsifier may be from about 0.001 to about 10% by weight, but preferably will range from about 0.01 to about 5% by weight, and most preferably about 0.1 to about 1% by weight, based upon the total weight of the composition. The emulsifier may be ionic, zwitterionic, or nonionic. Suitable emulsifiers include those of the polyethoxylated type (e.g., polyoxyethylene ethers or esters), polydiorganosiloxane-polyoxyalkylene block copolymers (e.g., dimethicone copolyol), Steareth-20, Steareth-21, fatty alcohols (e.g., Cetearyl Alcohol), Polyoxethylene sorbitan fatty acid esters (i.e., polysorbates), and Hydrogenated Castor Oil, to name a few. Additional emulsifiers are provided in the INCI Ingredient Dictionary and Handbook 11th Edition 2006, the disclosure of which is hereby incorporated by reference.

The compositions may further include an additional gelling agent. The gelling agent may comprise, for example, a silicone resin, including Dimethicone/Vinyl Dimethicone crosspolymer, silicone T-resins, ETPEA, polyamides, cellulose ethers (e.g., methyl cellulose or ethyl cellulose) and the like. Thickeners such as acrylates copolymers, hydroxyalkyl cellulose, carboxymethylcellulose, carbomers, and vegetable gums such as xanthan gum may be included.

The compositions may also comprise humectants (in addition to the polyol) such as polyols (e.g., glycols), including without limitation, glycerin, propylene glycol, ethoxydiglycol, butylene glycol, pentylene glycol, hexylene glycol, caprylyl glycol, and the like. These may be added in amount, for example, from about 0.001 to about 5% by weight of the composition.

In some embodiments, the compositions may comprise one or more of optical modification particles (e.g., soft focus particles), waxes, vegetable oils, esters, and fatty alcohols/acids.

The compositions of the invention may optionally include additional skin benefit agents such as skin penetration enhancers; emollients (e.g., isopropyl myristate, petrolatum, dimethicone oils, ester oils, mineral oils, or hydrocarbon oils); skin plumpers (e.g., palmitoyl oligopeptide), humectants (e.g., polyols, including propylene glycol, glycerin, etc.); antioxidants (e.g., BHT, ascorbic acid, sodium ascorbate, ascorbyl palmitate, beta-carotene, thiodipropionic acid, vitamin E, etc.); vitamins (e.g., tocopherol, tocopheryl acetate, etc.); alpha-hydroxy acids (e.g., glycolic acid), beta-hydroxy acids (e.g., salicylic acid); retinoids (e.g., retinoic acid, all-trans-retinoic acid, retinaldehyde, retinol, and retinyl esters such as acetates or palmitates); other anti-aging ingredients (e.g., collagen stimulators, collagenase inhibitors, elastase inhibitors); depigmenting agents (e.g., TDPA, hydroquinone, kojic acid, etc.); exfoliating agents (e.g., glycolic acid, 3,6,9-trioxaundecanedioic acid, etc.); estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few. The amounts of these various substances are those that are conventionally used in the cosmetic/personal care fields to achieve their intended purposes, for example, they may constitute from about 0.001 weight % to about 20 weight % of the total weight of the composition.

The compositions may also optionally include one or more of anti-allergenics; anti-fungals; antiseptics; anti-irritants; anti-inflammatory agents; antimicrobials; anti-bacterials; and analgesics in an amount from about 0.001 weight % to about 20 weight % of the total weight of the composition.

In some embodiments, the compositions comprise one or more of anti-perspirants and deodorants.

A sunscreen may be included to protect the skin from damaging ultraviolet rays. In one embodiment, the sunscreen provides both UVA and UVB protection, by using either a single sunscreen or a combination of sunscreens. Among suitable sunscreens are avobenzone, cinnamic acid derivatives (such as octylmethoxy cinnamate), octyl salicylate, oxybenzone, octocrylene, titanium dioxide, zinc oxide, or any mixtures thereof. The sunscreen may be present from about 1% to about 30% by weight of the total composition.

Other suitable components include those agents that provide a prophylactic or therapeutic benefit to skin. Particular mention may be made of alpha-hydroxy acids, beta hydroxyl acids, ascorbic acid or Vitamin C and derivatives thereof (e.g., $C_1$-$C_8$ esters thereof); retinoids such as retinol (Vitamin A) and the esters thereof (e.g., $C_1$-$C_8$ esters, such as palmitate), and hyaluronic acid.

Other suitable additives include vitamins, such as tocopherol and ascorbic acid; vitamin derivatives such as ascorbyl monopalmitate, tocopheryl acetate, and Vitamin E palmitate; metal chelating agents such as EDTA or salts thereof and pH adjusters (citric acid, ethanolamine, sodium hydroxide, etc.).

The compositions may also comprise a preservative or anti-microbial agent, for example, methylchloroisothiazolinone, methylisothiazolinone, methylparaben, propylparaben, phenoxyethanol, or caprylyl glycol.

Methods for providing prolonged delivery of a fragrance oil are also encompassed by the invention, comprising applying to a surface a composition of the invention. In some embodiments, the compositions are applied to a human integument, such as the skin of the face, hands, or body, or the hair of the scalp.

The compositions of the invention are capable of releasing a fragrance oil over a longer period of time as compared to otherwise identical compositions that lack either the hydrophilically-modified cross-linked silicone elastomer or the acrylic rheology modifier.

The composition can be applied as often as necessary to impart the desired fragrance intensity, cosmetic finish, color or appearance to the skin, etc. A composition according to the invention is expected to achieve extended release of fragrance oil for a long-wear period such as from about 1 to about 48 hours, from about 1 to about 24 hours or from about 1 to about 12 hours.

The composition may be suitably packaged in a container equipped with a pump dispenser, for example. The composition in such an embodiment is preferably in the form of a flowable gel having a rheology suitable for flowing during pumping and thickening after being deposited on the skin (e.g., a thixotropic rheology).

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, § 201(i).

EXAMPLES

Example 1

Three fragrance gels were prepared according to the formulas in Table 1. The inventive gel included both a hydrophilically-modified cross-linked silicone elastomer (PEG-12 dimethicone/PPG-20 crosspolymer) and an acrylic rheology modifier (hydroxyethyl acrylate/sodium acryloyldimethyltaurate copolymer). Gel A excluded only the PEG-12 dimethicone/PPG-20 crosspolymer and Gel B excluded only the hydroxyethyl acrylate/sodium acryloyldimethyltaurate copolymer. The fragrance oil in each of the formulations was limonene.

The hydrophilically-modified cross-linked silicone elastomer used in the formulations is sold as EL-7040 by Dow Corning, which also contains caprylyl methicone. EL-7040 contains 20% PEG-12 dimethicone/PPG-20 crosspolymer, so that PEG-12 dimethicone/PPG-20 crosspolymer was present in the inventive gel and in Gel B in an amount of 1.5% by weight of the total formulation. The acrylic rheology modifier used in the formulations is sold as Simulgel INS-100 by SEPPIC, which also contains isohexadecane and polysorbate 60. Simulgel INS-100 contains 37.5% hydroxyethyl acrylate/sodium acryloyldimethyltaurate copolymer, so that hydroxyethyl acrylate/sodium acryloyldimethyltaurate copolymer was present in the inventive gel and Gel A in an amount of 1.5% by weight of the total formulation.

TABLE 1

| Material | Inventive Gel (%) | Gel A (%) | Gel B (%) |
|---|---|---|---|
| Alcohol SD 40B Anhydrous | 41.75 | 45.50 | 43.75 |
| Glycerin | 41.75 | 45.50 | 43.75 |
| Fragrance Oil | 5.00 | 5.00 | 5.00 |
| PEG-12 dimethicone/PPG-20 crosspolymer and caprylyl methicone (EL-7040) | 7.50 | 0 | 7.50 |
| Hydroxyethyl acrylate/sodium acryloyldimethyltaurate copolymer and isohexadecane and polysorbate 60 (Simulgel INS-100) | 4.00 | 4.00 | 0 |

A standard fragrance spray (hydro-alcoholic EDT spray) and a gelled version (with hydroxyethyl cellulose) of the hydro-alcoholic EDT spray were also prepared, each containing 5.0% by weight of the fragrance oil. All of the preparations were tested to assess the percent of fragrance retained in each formulation over a 24-hour period using headspace analysis. Each formulation assessed initially contained 5.0% by weight of a fragrance oil. The fragrance oil comprised an unknown percentage of limonene, but the same fragrance oil was used in each experiment. Test material (0.20 g) was placed inside the bottom of a 2 oz glass jar, and smoothed to an even coating. Samples were placed in a 100° F. water bath, and left uncovered for 0 hours or 24 hours. After 24 hours, the samples were covered with a vapor impervious film and left untouched for 30 minutes. Following 30 minutes, the samples were penetrated and 1 cc of headspace was drawn. The headspace was then analyzed via gas chromatography (GC). The percent of fragrance retention was calculated as integrated area of the limonene GC peak at 24 hours relative to initial limonene integrated area. The results of these experiments are displayed below in Table 2, as well as in FIG. 1.

TABLE 2

| | Inventive Gel | Gel A | Gel B | Hydro-alcoholic EDT Spray | Gelled hydro-alcoholic EDT Spray |
|---|---|---|---|---|---|
| % Retention (24 hr vs. initial) | 36.8% | 3.6% | 1.3% | 4.9% | 0.3% |

The standard hydro-alcoholic EDT spray retained 4.9% fragrance after 24 hours, and the gelled version of the hydro-alcoholic spray retained only 0.3% of the fragrance. Gel A, which contained PEG-12 dimethicone/PPG-20 crosspolymer but no hydroxyethyl acrylate/sodium acryloyldimethyltaurate copolymer, exhibited a fragrance retention of 3.6% after 24 hours. Gel B, which contained hydroxyethyl acrylate/sodium acryloyldimethyltaurate copolymer but no PEG-12 dimethicone/PPG-20 crosspolymer, exhibited a fragrance retention of 1.3% after 24 hours. The inventive gel that contained both the PEG-12 dimethicone/PPG-20 crosspolymer and the hydroxyethyl acrylate/sodium acryloyldimethyltaurate copolymer unexpectedly retained 36.8% fragrance after 24 hours. The striking increase in fragrance retention of the inventive gel is far greater than an additive effect of each of the PEG-12 dimethicone/PPG-20 crosspolymer and the hydroxyethyl acrylate/sodium acryloyldimethyltaurate copolymer, demonstrating a synergy between the two components.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

What is claimed:

1. A long-wearing composition for providing extended release of fragrance, said composition comprising:
   (a) from about 0.5% to about 5% by weight of a hydrophilically-modified cross-linked silicone elastomer;
   (b) from about 0.5% to about 5% by weight of an acrylic rheology modifier;
   (c) from about 20% to about 75% by weight of a polyol;
   (d) from about 20% to about 75% by weight of an alcohol; and
   (e) from about 2% to about 10% by weight of a fragrance oil, wherein the composition is capable of releasing said fragrance oil over a longer period of time as compared to an otherwise identical composition lacking either said hydrophilically-modified cross-linked silicone elastomer or said acrylic rheology modifier.

2. The composition according to claim 1, wherein said hydrophilically-modified cross-linked silicone elastomer comprises poly(alkylene oxide) chains grafted to a silicone backbone.

3. The composition according to claim 1, wherein said hydrophilically-modified cross-linked silicone elastomer comprises PEG-12 dimethicone/PPG-20 crosspolymer.

4. The composition according to claim 1, wherein said acrylic rheology modifier comprises a copolymer of an acrylate monomer and an acrylamide monomer.

5. The composition according to claim 1, wherein said acrylic rheology modifier comprises hydroxyethyl acrylate/sodium acryloyldimethyltaurate copolymer.

6. The composition according to claim 1, wherein said polyol comprises glycerin and said alcohol comprises ethanol.

7. The composition according to claim 1, wherein said fragrance oil comprises a blend of one or more fragrance oils.

8. The composition according to claim 1, wherein the weight ratio of said hydrophilically-modified cross-linked silicone elastomer and said acrylic rheology modifier is from about 2:1 to about 1:2.

9. The composition according to claim 1, further comprising one or more actives selected from the group consisting of: retinoids, hydroxyl acids, depigmenting agents, botanicals, collagenase inhibitors, elastase inhibitors, sunscreens, anti-perspirants, deodorants, anti-bacterias, and anti-fungals.

10. The composition according to claim 1, further comprising one or more colorants.

11. The method according to claim 1, wherein said surface is a human integument.

12. The composition according to claim 1, wherein the weight ratio of said polyol to said alcohol from about 2:1 to about 1:2.

* * * * *